United States Patent
Obata et al.

(10) Patent No.: US 9,400,333 B2
(45) Date of Patent: Jul. 26, 2016

(54) SURVEY METER

(75) Inventors: Toshiro Obata, Mitaka (JP); Hiraku Katsuyama, Mitaka (JP)

(73) Assignee: HITACHI ALOKA MEDICAL, LTD., Tokyo (JP)

(*) Notice: Subject to any disclaimer, the term of this patent is extended or adjusted under 35 U.S.C. 154(b) by 78 days.

(21) Appl. No.: 14/236,516

(22) PCT Filed: Jun. 14, 2012

(86) PCT No.: PCT/JP2012/065228
§ 371 (c)(1),
(2), (4) Date: Jan. 31, 2014

(87) PCT Pub. No.: WO2013/031334
PCT Pub. Date: Mar. 7, 2013

(65) Prior Publication Data
US 2015/0192680 A1  Jul. 9, 2015

(30) Foreign Application Priority Data
Sep. 1, 2011 (JP) .................. 2011-191064

(51) Int. Cl.
*G01T 1/161* (2006.01)
*G01T 1/16* (2006.01)
*A61B 6/00* (2006.01)

(52) U.S. Cl.
CPC . *G01T 1/16* (2013.01); *G01T 1/161* (2013.01); *A61B 6/4258* (2013.01)

(58) Field of Classification Search
CPC .............................. G01T 1/161; A61B 6/4258
See application file for complete search history.

(56) References Cited

U.S. PATENT DOCUMENTS

| | | | |
|---|---|---|---|
| 5,557,108 A | 9/1996 | Tumer | |
| 6,643,538 B1 * | 11/2003 | Majewski et al. | 600/436 |
| 6,771,802 B1 | 8/2004 | Patt et al. | |
| 7,173,244 B2 * | 2/2007 | Tomita et al. | 250/336.1 |
| 2005/0199818 A1 | 9/2005 | Tomita et al. | |
| 2011/0193186 A1 | 8/2011 | Yu et al. | |

FOREIGN PATENT DOCUMENTS

| | | |
|---|---|---|
| CN | 1653355 A | 8/2005 |
| EP | 1505409 A1 | 2/2005 |
| JP | 05-47882 A | 6/1993 |
| JP | 06273531 A * | 9/1994 |

(Continued)

OTHER PUBLICATIONS

International Search Report dated Jul. 10, 2012, issued in corresponding application No. PCT/JP2012/065228.

(Continued)

*Primary Examiner* — Christine Sung
(74) *Attorney, Agent, or Firm* — Westerman, Hattori, Daniels & Adrian, LLP (57) ABSTRACT

A survey meter according to the present invention is a portable radiation measurement device. The survey meter comprises a tip portion, an intermediate portion, and a grip portion. A display unit is provided on the top surface of the intermediate portion. The tip portion extends to the intermediate portion with a bent portion therebetween. The tip portion forms an inclined portion. The grip portion has a constricted portion. A radiation detection unit is provided inside the tip portion and is formed by a plurality of sensors arranged in the right-left direction.

15 Claims, 9 Drawing Sheets

(56) References Cited

FOREIGN PATENT DOCUMENTS

| | | |
|---|---|---|
| JP | 2001-004757 A | 1/2001 |
| JP | 2002-168957 A | 6/2002 |
| JP | 2005-077380 A | 3/2005 |
| JP | 2006-071338 A | 3/2006 |
| JP | 2009-025005 A | 2/2009 |
| WO | 01/79885 A2 | 10/2001 |

OTHER PUBLICATIONS

Extended European Search Report dated Dec. 22, 2014, issued in corresponding EP Patent Application No. 12827156.6 (6 pages).

Office Action dated Jul. 1, 2015, issued in counterpart Chinese application No. 2012800425744 (w/English translation) (17 pages).

* cited by examiner

SURVEY METER

TECHNICAL FIELD

The present invention relates to a survey meter, and particular to a survey meter for measuring, for example, radiation from an object and radiation in the environment.

BACKGROUND ART

A survey meter is a device for measuring, for example, radiation from objects (buildings, natural objects, human bodies, etc.) and radiation existing in the environment. The survey meter is typically configured as a portable device. The survey meter has a built-in radiation sensor, a measurement circuit, and a battery, and the radiation sensor and an electronic circuit are operated by electrical power from the battery. Survey meters disclosed in Patent Documents 1, 2, and 3 are each composed of a body having a box shape, and a detection section connected to the body via a cable. A handle attached to the body is held by one hand, and a grip of the detection section is held by the other hand.

CITATION LIST

Patent Documents

Patent Document 1: JP 2001-004757 A
Patent Document 2: JP 2005-077380 A
Patent Document 3: JP 2009-025005 A

SUMMARY OF INVENTION

Technical Problem

When the above conventional survey meter is used, there is a problem that both hands are always required. Thus, there has been a desire to realize a compact survey meter which can be held and operated with one hand. If a simple box-shaped survey meter is formed as such a survey meter, there may occur a problem that operability is poor, or that an indicator becomes less visible when a main measurement direction of the detection section is directed to an object. Further, although it is desirable to form a thin survey meter to improve operability, in that case, a space to install the detection section becomes smaller, and it becomes difficult to install a large sensor while directing a sensitive surface of the sensor to the object side. At least one of the above problems must be addressed.

Solution to Problem

The objective of the present invention is to provide a compact survey meter with good operability. Alternatively, the objective of the present invention is to provide a survey meter which can be held in one hand and easily carry out measurement, the survey meter having an indicator that can be easily seen during the measurement. Alternatively, the objective of the present invention is to reduce the thickness of an end portion (detection section) directed to the object while ensuring good sensitivity.

A survey meter according to the present invention has an intermediate portion which has a shape extended in the front-back direction and the right-left direction and a display section provided on a top surface thereof; a tip portion which has a shape extended in the right-left direction, connects to a front side of the intermediate portion via a bent portion, and contains a radiation detection section; and a grip portion which has a flat shape extended in the front-back direction and the right-left direction and connects to a rear side of the intermediate portion, and in the survey meter, the tip portion is a portion which is inclined from the bent portion to the bottom side.

With the above configuration, as the intermediate portion has a flat shape, a display surface (display section) can easily be provided on a top surface thereof. Alternatively, a large area can be ensured as a space for installing the display section. The tip portion containing the radiation detection section is connected to the front side of the intermediate portion via the bent portion, the tip portion being inclined to the bottom. Preferably, the tip portion is a portion extending obliquely downward from the front end of the intermediate portion. Therefore, if the tip portion is directed to an object, the display section is directed toward the operator who holds the survey meter, and thus, the display surface can be easily seen. In other words, with the above configuration, under various measurement conditions, the display surface can have a larger intersection angle with respect to the line of sight than when the tip portion is not inclined. The grip portion is connected to the rear side of the intermediate portion and held with the hand. Thus, the problem that the display section is hidden by the hand is overcome or alleviated. That is, when the grip portion is held with one hand, and the tip portion is directed to an object, the display surface is naturally directed to the user side, and the visibility of the display surface can be improved. In other words, radiation dose information can be read without moving the eyes or without largely moving the eyes during measurement. The visibility of an operation section can also be improved if it is provided on the top surface of the survey meter. Further, because the object, the tip portion, the display surface, the operation section, etc. can fall within the user's vision, the usability is greatly improved.

Preferably, the intermediate portion has a virtual first central axis passing through the intermediate portion in the front-back direction, and the tip portion has a virtual second central axis that is identical to a main measurement direction. The first central axis and the second central axis intersect in the bent portion, and an intersection angle between the first central axis and the second central axis is set to fall within a range of 10 to 60 degrees. More preferably, the intersection angle is set to fall within a range of 15 to 45 degrees. These numerical values are obtained from experiments and experience, etc. It is preferable to select an appropriate bend angle depending on the intended use. The survey meter may be configured such that the bend angle can be changed.

Preferably, the intermediate portion and the grip portion are integrally connected, and the intermediate portion and the tip portion are integrally connected. The intermediate portion and the grip portion have substantially the same thickness and form a flat plate shape as a whole. The tip portion has a shape extended in the second central axis direction and the right-left direction, and has a tip end surface that is orthogonal to the second central axis. According to this configuration, each portion has a flat shape and, the survey meter as a whole has a general shape like that of a remote control unit for a television, audio equipment, etc. However, the shape of the above survey meter differs from that of a general remote control unit in that, in the survey meter, the main measurement direction (the front direction used as a reference direction during calibration or the main sensitivity direction) intersects the first central axis; that is, the tip portion is inclined. The general remote control unit is directed to the horizontal direction when it is used, and is not directed obliquely upward at an angle of 45 degrees and is not directed to the floor (for example, obliquely downward at an angle of 45 degrees).

Preferably, the grip portion has a constricted shape when seen from above. When the constricted shape is adopted, the survey meter is easy to hold, and the display surface is not easily hidden by the hand because a portion to be held is clear. Preferably, the tip portion has a tapered shape when seen from above. Preferably, the grip portion has an operation section on a top surface thereof. Preferably, the grip portion is gripped by placing the palm on one side surface of the grip portion, while placing the thumb on the top surface, and holding the other side surface of the grip portion with the remaining four fingers. Holding the grip portion in such a manner allows the operation section provided on the top surface to be operated with the thumb. That is, the survey meter can be both gripped and operated with one hand. Of course, it is preferable to change a way to hold the survey meter according to the height and orientation of the object to be measured and a measurement orientation of the survey meter.

Preferably, the radiation detection section includes a plurality of sensors arranged in the right-left direction. As the tip portion has a shape extended in the right-left direction, it is reasonable to arrange a plurality of sensors in the right-left direction in accordance with the shape. That is, it is possible to achieve good space efficiency. Preferably, the radiation detection section includes a filter member that wraps the plurality of sensors. The filter member has a function to improve an energy sensitivity characteristic and/or a function to enhance the sensitivity in the main measurement direction (improve the sensitivity characteristic) of the radiation detection section as a whole. In a preferred embodiment, the filter member functions as a scatterer, and, even when the sensitive surface of the semiconductor sensor is not directed to the main measurement direction, the sensitivity can be enhanced in the main measurement direction. Assuming that the surface directed to the main sensitivity direction is the front surface, the filter member is preferably provided on not only the front surface but also the four side surfaces. The filter member may also be provided on the back surface. A plurality of types of filter members may be used. The thickness of the filter member may be different for each surface. Further, the filter member may be provided so as to provide collimating action.

Preferably, each sensor is a flat plate semiconductor sensor having a sensitive surface, and when a main measurement direction is defined as a direction which is orthogonal to the right-left direction and to which the tip portion is directed, and when a tip portion thickness direction is defined as a direction which is orthogonal to the right-left direction and the main measurement direction, the sensitive surface of each sensor is directed to the right-left direction or the tip portion thickness direction. Preferably, the plurality of sensors are layered in the right-left direction. With this configuration, it is possible to from a laminated body and increase the sensitive area. Preferably, the laminated body is composed of sensors of identical shape. If the sensor has a front surface and a back surface, the sensors may be arranged so that they are oriented symmetrically on the right and left sides. Preferably, the plurality of sensors are arranged in the right-left direction so that sensitive surfaces thereof are directed to the tip portion thickness direction. With this configuration, the extended direction of the tip portion is combined with the extended direction of the detection surface, to thereby enhance space efficiency. A plurality of sensors of different sizes may be arranged.

Preferably, there is provided a control section which selects, from the plurality of sensors, one or more sensors which are caused to perform detection operation according to an amount of radiation. When, under the high dose of radiation, pulses continue and are saturated, this control section reduces the number of operating sensors and prevents such saturation.

DESCRIPTION OF EMBODIMENTS

A preferable embodiment of the present invention will be described by reference to the drawings.

Figure 1:
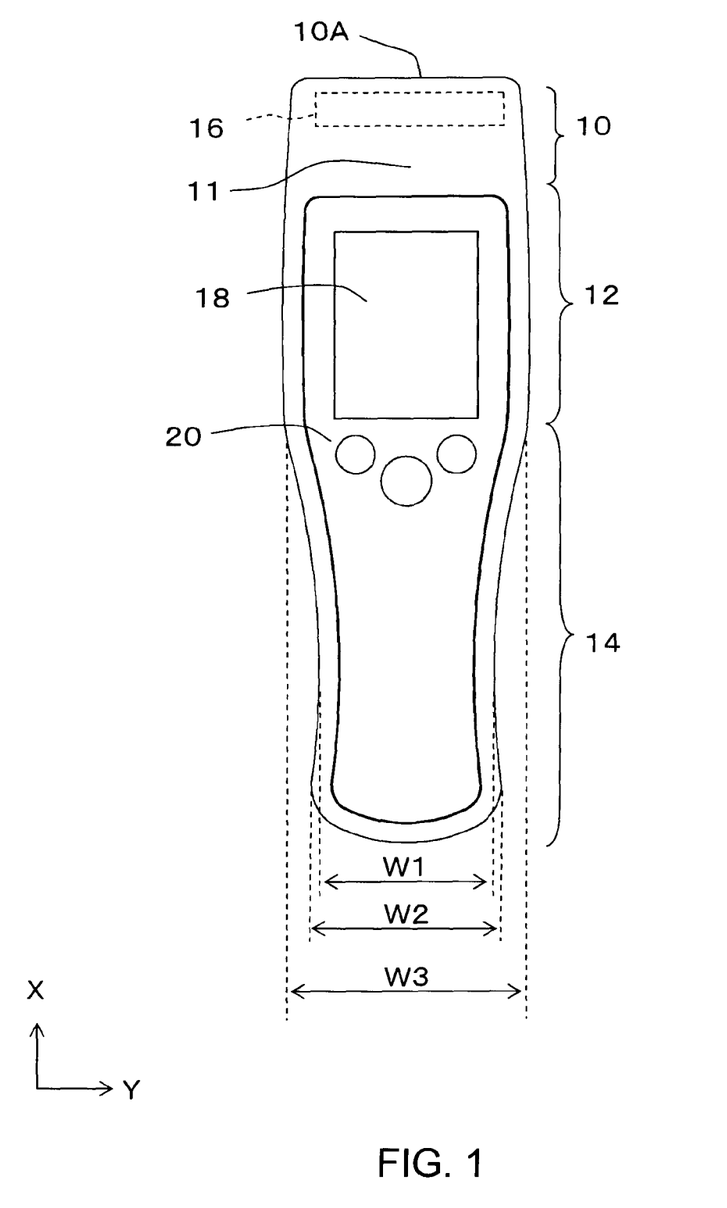
FIG. 1 shows a preferable embodiment of a survey meter according to the present invention.

FIG. 1 shows a preferable embodiment of the survey meter according to the present invention, and FIG. 1 shows a top view of the survey meter. This survey meter is a radiation measuring device for measuring radiation from objects, such as buildings and human bodies. Of course, radiation in the environment and other types of radiation may be measured. Although, in the present embodiment, γ-rays are measured, other types of radiation may also be measured.

In FIG. 1, the survey meter has a built-in battery and is configured as a portable device. In the present embodiment, the survey meter is configured such that the survey meter can be operated while being held in one hand. The survey meter has three sections from the fore end side to the back end side; more specifically, it has a tip portion 10, an intermediate portion 12, and a grip portion 14. The intermediate portion 12 has a display section 18 on the top surface thereof. The display section 18 is composed of a liquid crystal indicator and the like. The intermediate portion 12 has a flat shape extended in the X direction and the Y direction; that is, it has a flat plate shape. The X direction is a front-back direction, and the Y direction is a right-left direction. The intermediate portion 12 and the grip portion 14 have a thickness of, for example, 17.5 mm. Preferably, the thickness is selected from a range of 10 to 25 mm.

The tip portion 10 is integrally connected to the front side of the intermediate portion 12 via a bent portion 11. The tip portion 10 forms an inclined portion which is inclined to the bottom surface side of the intermediate portion 12 as described below. As shown in the figure, the tip portion 10 has a shape extended in the right-left direction (Y direction). More specifically, the tip portion 10 has a flat shape extended in both the main measurement direction (described later) and the right-left direction (Y direction). The tip portion 10 has a thickness of, for example, 20 mm in a direction orthogonal to both the right-left direction and the main measurement direction. Preferably, the thickness is selected from a range of, for example, 15 to 30 mm.

The tip portion 10 has a detection section 16 therein. In the present embodiment, the detection section 16 is configured to include a plurality of semiconductor sensors as described below. An end surface of the tip portion 10; that it, a tip surface 10A, is a detection surface and forms a surface orthogonal to the main measurement direction. As shown in FIG. 1, the tip portion 10 has a slightly tapered shape when seen from above.

The grip portion 14 is a portion gripped by the hand of the user. The grip portion 14 has a constricted shape when seen from above. Similar to the intermediate portion 12, the grip portion 14 has a flat shape extended in the X direction and the Y direction; that is, a flat plate shape. The width W3 in the Y direction at the front edge of the grip portion 14 is largest in the Y direction, and when the width is observed from that point to the back end direction, the width once becomes W1 in the intermediate portion and then extends again and becomes W2 at the rear edge. As described above, the grip portion 14 has a constricted shape when seen from above. This allows the grip portion 14 to be easily held, and overcomes or alleviates the problem that the display section 18 is covered by the hand when the grip portion 14 is gripped.

There is provided an operation section 20 on the top surface of the grip portion 14; more specifically, on the rear side of the display section 18 on that top surface. In the present embodiment, the operation section 20 is composed of three push buttons. How to grip the grip portion 14 will be explained. When, for example, it is gripped by the right hand, the palm is placed on the right side surface of the grip portion 14, while the right thumb is placed on the top surface of the grip portion 14, and the remaining four fingers of the right hand hold the left side surface of the grip portion 14. The operation section 20 is operated in such a state. Of course, the grip portion 14 may be held in various ways depending on, for example, a location of the object, an orientation of the object, and the user's preference.

It is preferable to provide a jacket made of an elastic material for wrapping the entire survey meter. With such a jacket, it is possible to protect a housing of the survey meter and electronic components therein, even if the survey meter is dropped by mistake. Such a jacket is preferably configured to be detachable. FIG. 1 shows the X direction and the Y direction. There is the Z direction which is defined as a direction orthogonal to them. The Z direction is a thickness direction of the intermediate portion 12 and the grip portion 14.

Figure 2:
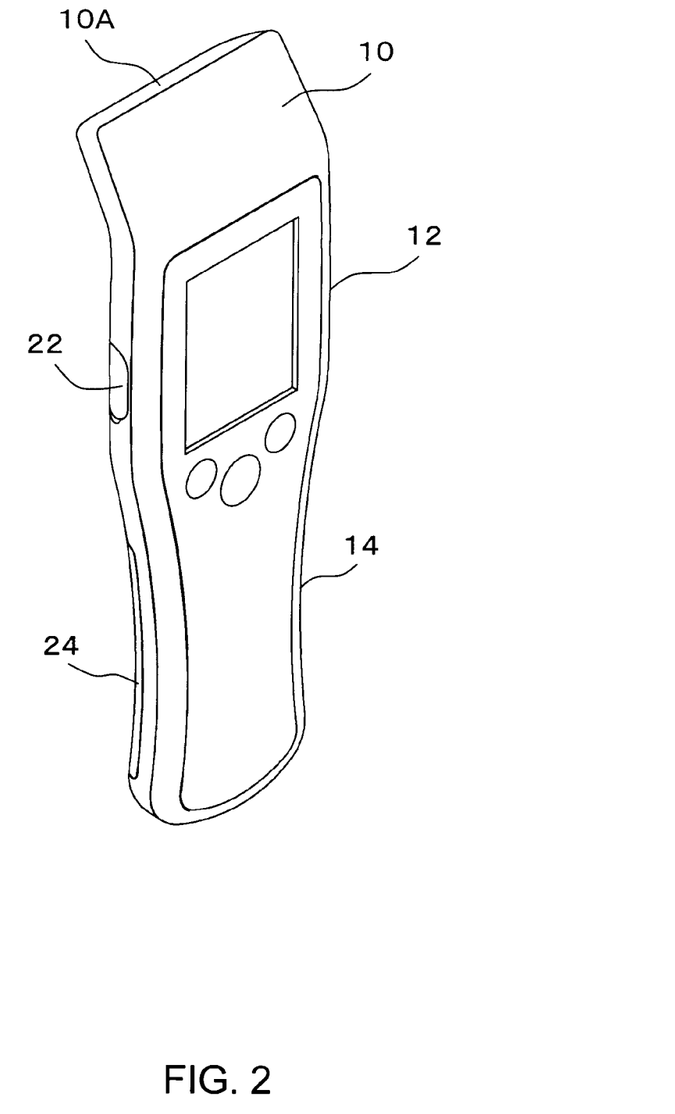
FIG. 2 shows a perspective view of the survey meter shown in FIG. 1.

FIG. 2 shows a perspective view of the above survey meter. As described above, the survey meter has, from the tip end to the back end thereof, the tip portion 10, the intermediate portion 12, and the grip portion 14. The tip surface of the tip portion 10 forms the detection surface 10A, and the detection surface 10A is orthogonal to the main measurement direction. Here, the main measurement direction is a reference direction for calibration or the most sensitive direction. The main measurement direction is a direction toward which the tip portion 10 is directed. A component 22 is a USB port. A component 24 is a cover of a battery case. In the present embodiment, it is possible to charge the battery via the USB port.

Figure 3:
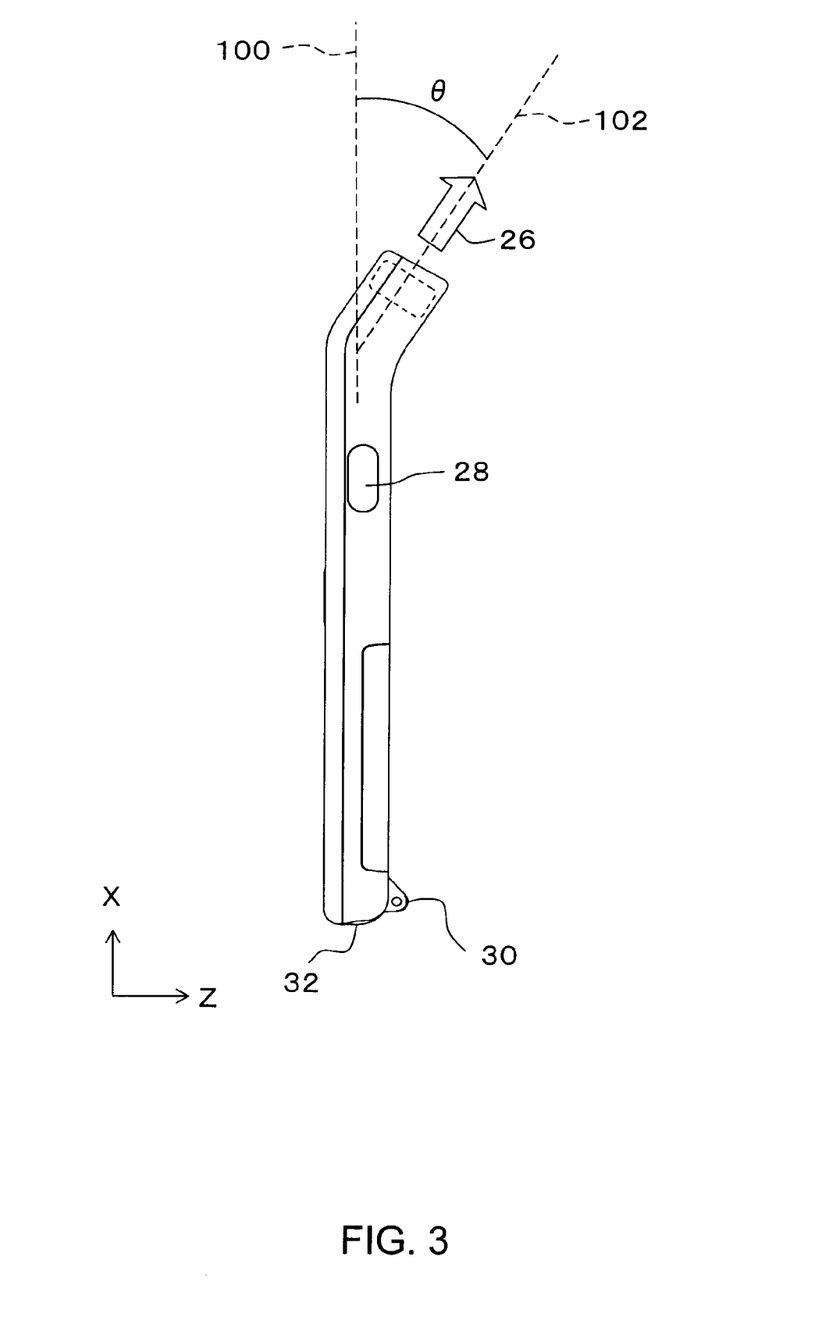
FIG. 3 shows a right side view of the survey meter shown in FIG. 1.

FIG. 3 shows the right side surface of the survey meter. A line 100 indicates the central axis passing through the center of the intermediate portion and the grip portion, and a line 102 indicates the central axis passing through the tip portion. The central axis 102 is identical to the main measurement direction 26. An intersection angle θ between the central axis 100 and the central axis 102 is preferably set within a range of 10 to 60 degrees, and more preferably, is set within a range of 15 to 45 degrees. In the present embodiment, it is set at 30 degrees. As described above, the intermediate portion and the grip portion have a thickness of, for example, 17.5 mm in the Z direction, and the tip portion has a thickness of, for example, 20 mm in the direction orthogonal to the central axis 102. Of course, the numerical values described herein are merely examples. In any case, it is preferable to form the survey meter such that it can be easily gripped by one hand and operated by one hand.

The shape of the survey meter shown in FIGS. 1 to 3 is similar to the shape of a remote controller which comes with a TV or audio equipment. However, such a remote controller is not directed to the floor surface or upper portion of the wall surface, but is directed to the generally horizontal direction. On the other hand, the survey meter of the present embodiment can measure, for example, radiation contamination on the floor surface and the upper portion of the wall surface, and in consideration of such usage, the above-described bent shape is adopted. For example, when the detection surface is directed to the floor surface, the display surface of the display section is naturally directed to the user side. Even if the display surface does not face the front of the user side, the angle formed between the display surface and a line of sight can be relatively large, and therefore, the visibility of the display surface can be improved. In addition, the display surface is exposed while the grip portion is being held, and the display section, the tip portion, and an object portion can be easily seen in the same visual field. As such, there can be obtained an advantage that the user can carry out measurement while simultaneously observing the object portion and the display surface. Thus, the survey meter according to the present embodiment is compact and has excellent usability. As shown in FIG. 3A, a protruding portion 30 for attaching a strap may be provided. Further, an earphone jack 32 may be provided to listen to pulse sound of the radiation detector using an earphone.

Figure 4:
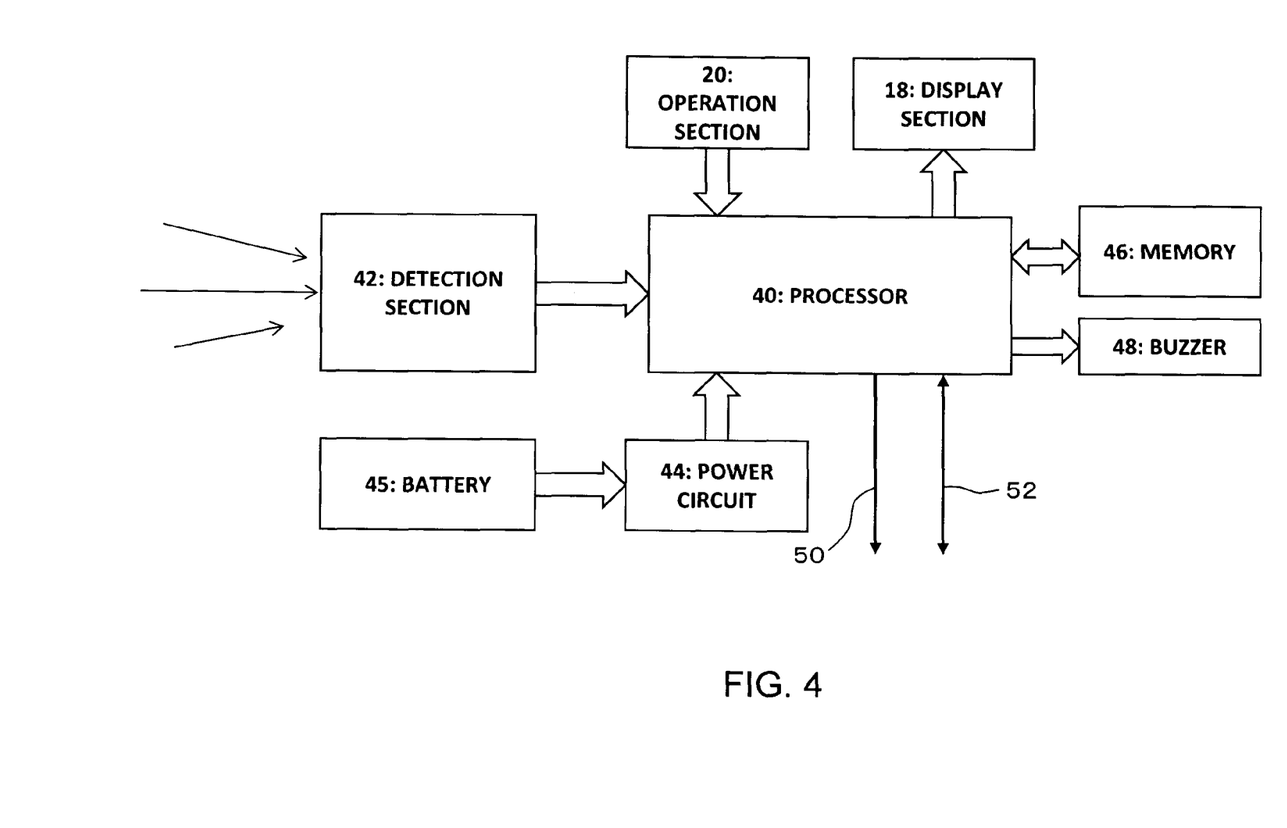
FIG. 4 shows a block diagram showing a configuration of the survey meter shown in FIG. 1.

FIG. 4 shows a block diagram of a circuit configuration in the above-described survey meter. A processor 40 is composed of one or more microcomputers and carries out signal processing and operation control. A detection section 42 is connected to the processor 40. A configuration of this detection section 42 will be described below by reference to FIGS. 5-8. The processor 40 is connected to the operation section 20 and the display section 18. As described above, the operation section 20 is composed of the three buttons. As described above, the display section 18 is composed of a liquid crystal panel. The display section 18 and the operation section 20 may be integrated, to thereby form a touch screen. Further, the processor 40 is connected to a memory 46. An external memory may be provided. A buzzer 48 is provided to produce alarm calls. An arrow 50 indicates an output signal to the earphone, and an arrow 52 indicates an access signal to/from the outside via the USB port. In addition to these components, a GPS system may further be incorporated. A battery 45 supplies electrical power to each component included in the survey meter. More specifically, electrical power is supplied from the battery 45 to each component via a power circuit 44. The configuration shown in FIG. 4 is merely an example.

Figure 5:
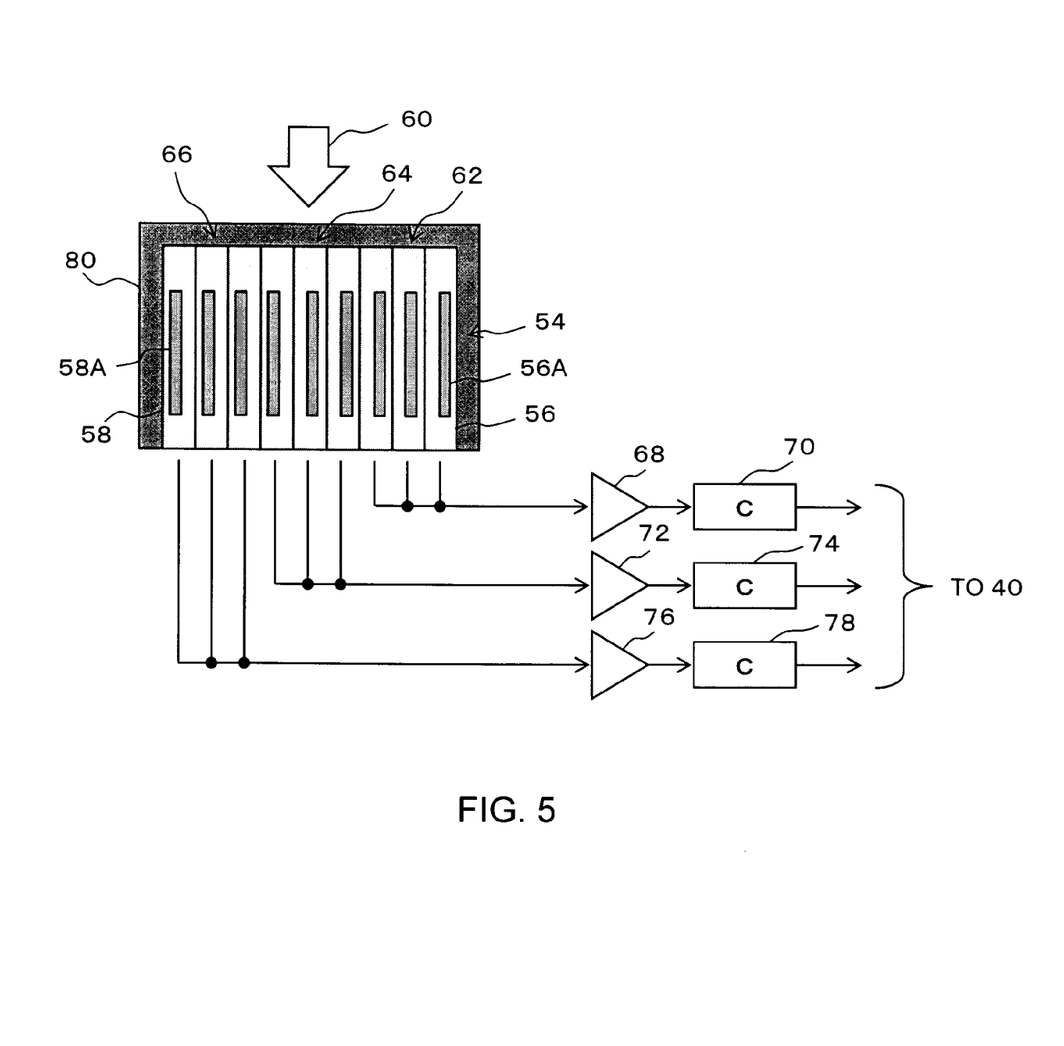
FIG. 5 shows a first example of a radiation detection section.
Figure 6:
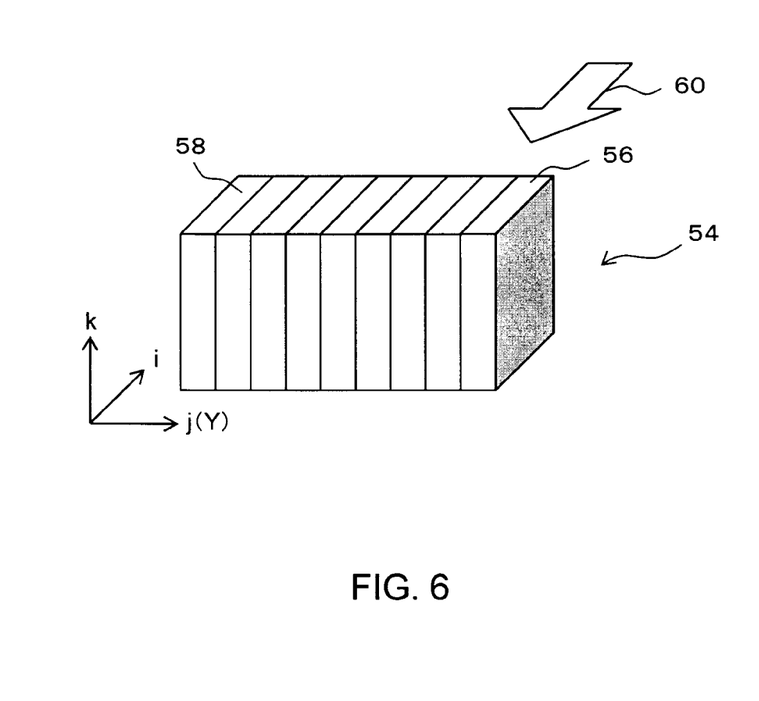
FIG. 6 shows a first example of the radiation detection section.

FIG. 5 and FIG. 6 illustrate a first example of the radiation detection section.

In FIG. 5, a laminated body 54 is composed of a plurality of sensors 56 and 58 and, more specifically, nine semiconductor sensors layered in the right-left direction; i.e., the Y direction. The sensors 56 and 58 have a flat plate shape and, more specifically, a shape extended in both the main measurement direction 60 and the tip portion thickness direction. Each sensor has a sensitive surface 56A or 58A. Generally, in each of the sensors 56 and 58, one surface thereof has a sensitivity characteristic that differs from that of the other surface. In consideration of this fact, in the present embodiment illustrated in this figure, approximately half of the semiconductor sensors—that is, five out of nine sensors—are arranged to the right, and the remaining approximate half—that is, four sensors—are arranged to the left. Thus, it is possible to obtain approximately uniform sensitivity in the plurality of sensors 56 and 58 as a whole with respect to the right-left direction.

In the present embodiment, the nine sensors 56 and 58 are divided into three groups. Here, one group is composed of three sensors. As such, a first group 62, a second group 64, and a third group 66 are produced. Three output signals from the first group 62 are added, and this addition signal is transmitted to a comparator 70 via an amplifier 68. The comparator 70 extracts, from the addition signal, only a signal portion that exceeds a predetermined threshold value and generates an output pulse based on this signal portion. This pulse is output to the processor 40 shown in FIG. 4. Similarly, an addition signal from the second group 64 is also output to the processor 40 via an amplifier 72 and a comparator 74. Further, an addition signal from the third group 66 is also output to the processor 40 via an amplifier 76 and a comparator 78. Providing three groups enables reduction of the scale of the electronic circuit and selection of the number of groups to be operated according to the amount of radiation. Of course, the sensors may be switched on and off individually without making groups.

In the present embodiment, a laminated body 54 is wrapped by a filter member 80. Among six surfaces of the laminated body 54, the filter member 80 is provided on the front surface directed to the main measurement direction 60 and the four side surfaces. Although, in the present embodiment, the filter member is not provided on the remaining back surface, it is, of course, possible to provide the filter member thereon. The filter member 80 is provided to achieve a good energy sensitivity characteristic. In the present embodiment, this filter member is made of copper. Of course, other materials or a combination of materials may be used to form the filter member 80. In the present embodiment, the laminated body 54 is wrapped by the filter member 80, and when γ-rays are scattered on the filter member 80, the scattered γ-rays are detected by the plurality of sensitive surfaces. According to the experiments, with the configuration of the detection section shown in FIG. 5, it is possible to align the main sensitivity in the main measurement direction 60. Of course, a certain level of sensitivity can also be obtained in the circumferential direction which is orthogonal to the main sensitivity direction.

FIG. 6 shows a perspective view of the above-described laminated body 54. In this figure, the j direction is the right-left direction; i.e., the Y direction, which is the lamination direction. The i direction is identical to the main sensitivity direction 60. The k direction is orthogonal to the i direction and the j direction and is identical to the tip portion thickness direction. The sensitive surfaces of the sensors extend in the i direction and the k direction. Although, generally, there is not much sensitivity in the main sensitivity direction 60 in such an arrangement, in the present embodiment, the above-described laminated structure enables the front surface to have sufficient sensitivity. In addition, the sum of the sensitive surfaces of the individual sensors becomes considerably large, and this results in improvement of the sensitivity.

Figure 7:
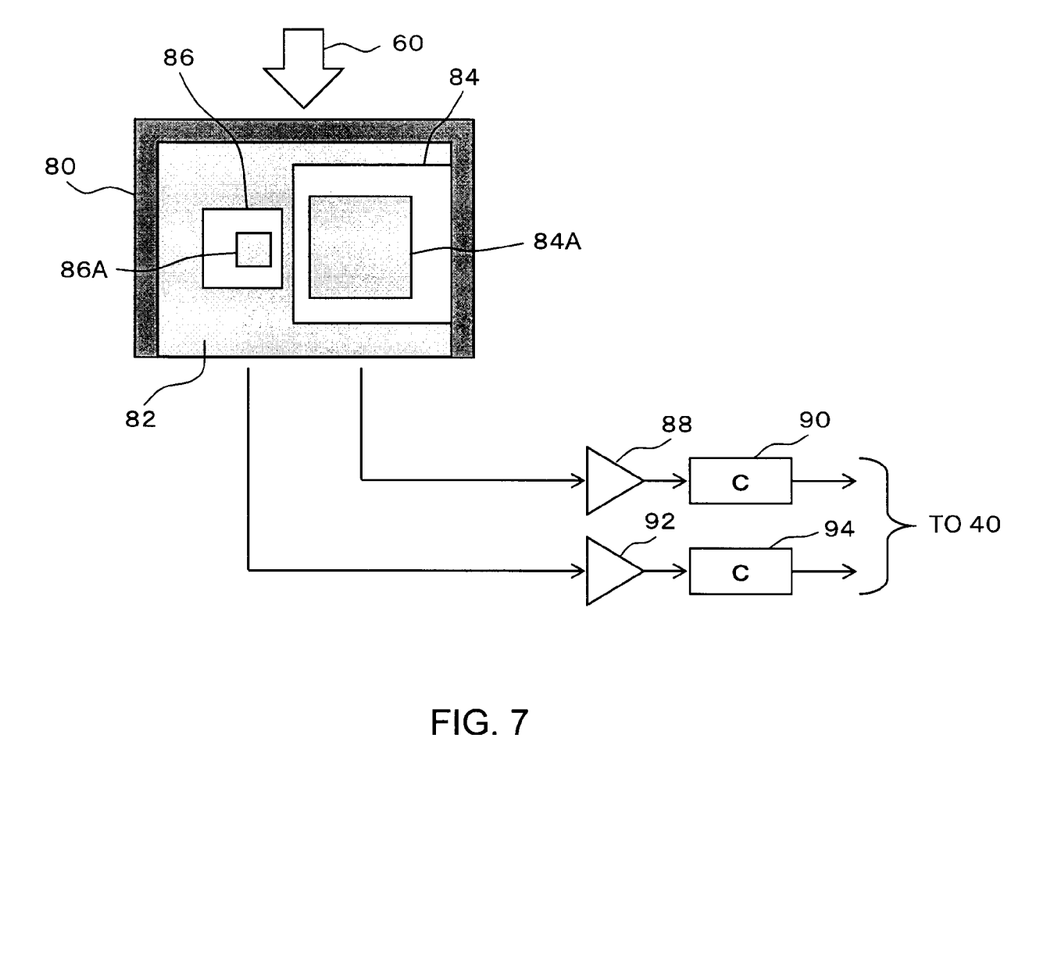
FIG. 7 shows a second example of the radiation detection section.
Figure 8:
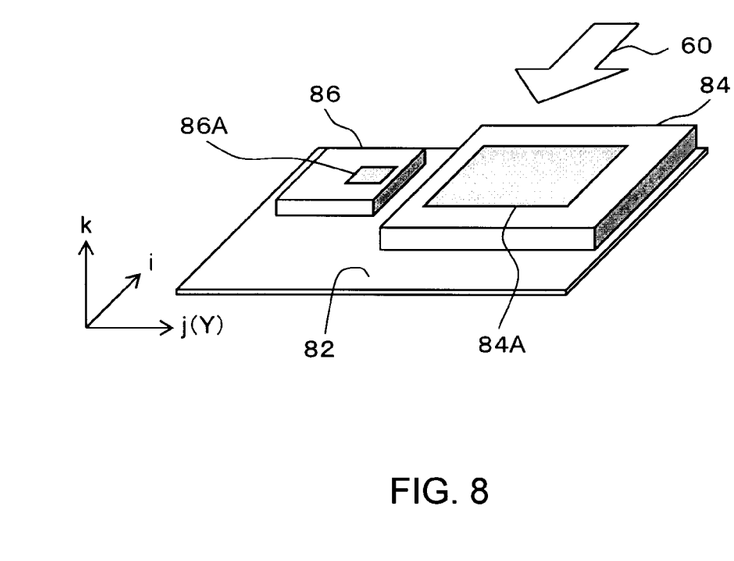
FIG. 8 shows the second example of the radiation detection section.

FIG. 7 and FIG. 8 show other example configurations of the radiation detection section.

In FIG. 7, two sensors 84 and 86 are provided on a substrate 82. The sensor 84 is a semiconductor sensor having a large area, and its sensitive surface 84A has a size of, for example, 10×10 mm. On the other hand, the sensor 86 is a relatively small semiconductor sensor, and its sensitive surface 86A has a size of 3×3 mm. The sensors shown in FIG. 5 also have the same size as the sensor 86. The sensitive surfaces 84A and 86A of the two sensors 84 and 86 are directed upward along the tip portion thickness direction.

Again, in this configuration example, the filter member 80 is provided around the circumference of the two sensors 84 and 86. This filter member 80 has the same form as the filter member shown in FIG. 5. The filter member 80 improves the energy sensitivity characteristic. Further, the filter member is also understood to function as a scatterer. From experiments, it is confirmed that, with such a configuration of the detection section, sufficient sensitivity can be obtained in the main measurement direction 60. However, it is also confirmed that, with this configuration shown in FIG. 7, the sensitivity increases in the right-left direction, depending on circumstances. It is, of course, possible to suppress such a rise in the sensitivity using other components.

An output signal of the first sensor 84 is transmitted to the processor 40 via an amplifier 88 and a comparator 90. Further, an output signal of the second sensor 86 is output to the processor 40 via an amplifier 92 and a comparator 94. Both or one of the two sensors 84 and 86 can be operated under control of the processor 40. Thus, it is possible to select the number or kinds of sensors to be operated according to the amount of radiation.

FIG. 8 shows a perspective view of the two sensors 84 and 86. As described above, the two sensors 84 and 86 are aligned on the substrate 82 in the right-left direction; i.e., the j direction. As described, the tip portion has a flat shape extended in the i direction and the j direction, and therefore, arranging the two sensors in this manner enhances space efficiency. It is in any case possible to obtain an advantage of achieving an extremely reasonable sensor arrangement in the tip portion by aligning the sensors in the right-left direction.

Figure 9:
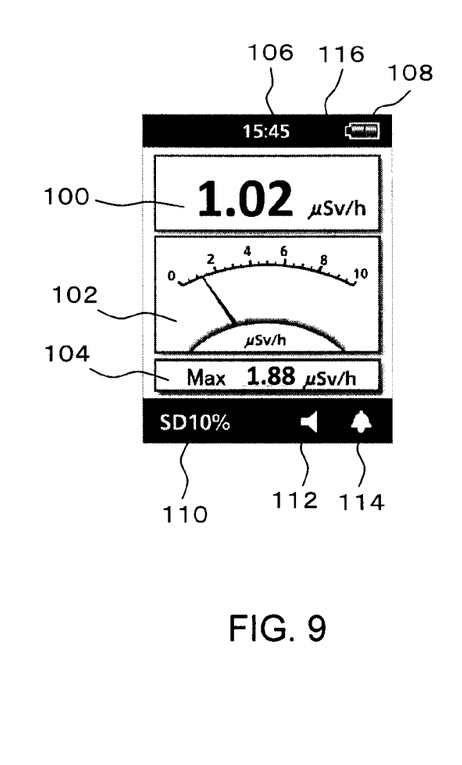
FIG. 9 shows a first display example.

Next, some display examples will be described by reference to FIG. 9 to FIG. 11. The survey meter according to the present embodiment has some display modes. In the display mode shown in FIG. 9, a dose equivalent rate is indicated by a numerical value 100 and a virtual analog meter 102. An integrated dose equivalent value, dose rate, integrated dose value, etc. may also be displayed. Reference numeral 104 indicates a maximum value of the dose equivalent rate which is obtained by tracing the rate back to the past. In other words, the survey meter of the present embodiment has a function of identifying a maximum value by tracing the rate back to the past. In this case, a period during which the rate is traced back may be specified by the user. Reference numeral 106 indicates the current time, and reference numeral 108 indicates a remaining battery level. Reference numeral 110 indicates a condition when a standard deviation is used for data computation, and reference numeral 112 indicates an ON/OFF state of a speaker. Reference numeral 114 indicates an ON/OFF state of a buzzer. Reference numeral 116 indicates an operation state of the device. If, for example, an operation of storing information in the memory is being carried out, it is in a predetermined light emitting state.

Figure 10:
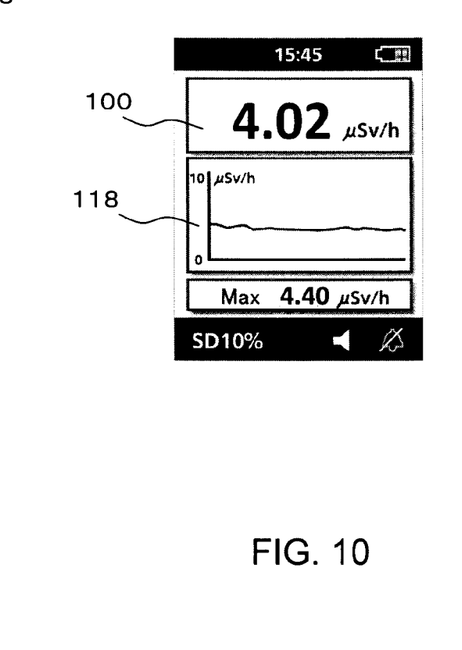
FIG. 10 shows a second display example.
Figure 11:
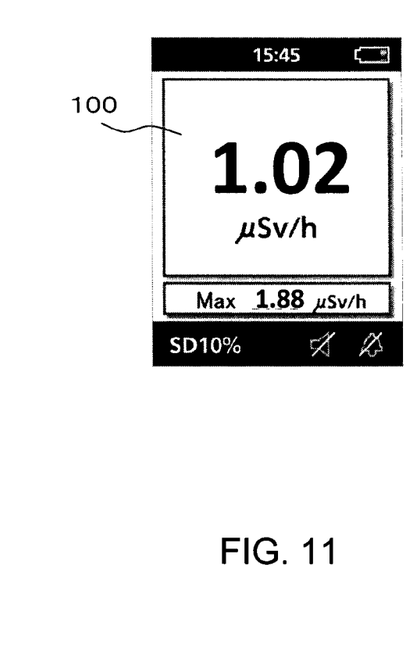
FIG. 11 shows a third display example.

In the display mode shown in FIG. 10, the current dose equivalent rate is displayed as indicated by reference numeral 100, and a trend graph is also displayed as indicated by reference numeral 118. This trend graph indicates changes of the dose equivalent rate by tracing the rate from the present back to the past. The graph may indicate changes of an integrated dose value. FIG. 11 indicates a still another display mode, and, in this example, a dose equivalent rate is indicated by a numerical value, as indicated by reference numeral 100.

With the above-described survey meter, it is possible to obtain advantages that all components are basically contained in a single case (all-in-one structure), and that measurement can be carried out by holding the case with one hand. Thus, the other hand can perform other operations. In addition, because the tip portion forms an inclined portion, and the grip portion is provided on the back end side, the detection surface of the survey meter can be naturally directed to the object when the survey meter is held, and the display surface is also easily observed in this state. In addition, as the grip portion has the constricted shape, it is possible to obtain an advantage that a portion to be gripped can be recognized correctly and that the portion is easy to grip. When the survey meter is held, the operation section can easily be operated by the thumb, etc., and, in that case, the display section is also prevented from being hidden by the hand. Further, the detection section has the flat shape, and a plurality of sensors are arranged in the right-left direction in accordance with the shape. Space efficiency is enhanced, and thus, detection sensitivity is enhanced.

In the present embodiment, the processor 40 shown in FIG. 4 switches the number of sensors to be operated according to the amount of radiation. Specifically, in the configuration example shown in FIG. 5 and FIG. 6, if the amount of radiation is low, the three groups are operated, while if the amount of radiation is high, only the central group is operated. Of course, the number of groups to be used may be changed in a smaller, step-by-step fashion. Further, in the configuration example shown in FIG. 7 and FIG. 8, if the amount of radiation is low, both the sensor 84 and the sensor 86 are operated, and if the amount of radiation is high, only the sensor 86 is operated. Further, if the amount of radiation is medium, only the sensor 84 may be operated. A person skilled in the art can change the present embodiment in various manners.

The invention claimed is:

1. A survey meter comprising:
an intermediate portion which has a shape extended in a front-back direction and a right-left direction and a display section provided on a top surface thereof;
a tip portion which has a shape extended in the right-left direction, connects to a front side of the intermediate portion via a bent portion, and contains a radiation detection section; and
a grip portion which has a flat shape extended in the front-back direction and the right-left direction and connects to a rear side of the intermediate portion, wherein
the tip portion is rearwardly inclined from the bent portion toward a bottom surface side of said intermediate portion,
the tip portion is rigidly and non-movably fixed to said intermediate portion via said bent portion with said bent portion rigidly maintaining a constant rearwardly inclined angle between said tip portion and said intermediate portion,
the grip portion is rigidly and non-movably fixed to said intermediate portion,
the intermediate portion has a virtual first central axis passing through the intermediate portion in the front-back direction;
the tip portion has a virtual second central axis that is identical to a main measurement direction;
the first central axis and the second central axis intersect in the bent portion; and
an intersection angle between the first central axis and the second central axis defines said rearwardly inclined angle and is set at a non-movable fixed angle that is within a range of 15 to 45 degrees.

2. The survey meter according to claim 1, wherein:
the intermediate portion and the grip portion are integrally connected, and the intermediate portion and the tip portion are integrally connected;
the intermediate portion and the grip portion have substantially a same thickness and form a flat plate shape as a whole; and
the tip portion has a shape extended in the second central axis direction and the right-left direction and has a tip end surface that is orthogonal to the second central axis.

3. The survey meter according to claim 2, wherein the grip portion has a constricted shape when seen from above.

4. The survey meter according to claim 2, wherein the tip portion has a tapered shape when seen from above.

5. The survey meter according to claim 1, wherein the grip portion has an operation section on a top surface thereof.

6. The survey meter according to claim 1, wherein:
the radiation detection section includes a plurality of sensors arranged in the right-left direction.

7. The survey meter according to claim 6, wherein the radiation detection section includes a filter member which wraps the plurality of sensors.

8. The survey meter according to claim 7, wherein said filter member which wraps the plurality of sensors is constructed to improve energy sensitivity and said filter member covers a front surface of said plurality of sensors to a main measurement direction and four side surfaces around said plurality of sensors adjacent said front surface.

9. The survey meter according to claim 8, wherein said filter is made with copper.

10. The survey meter according to claim 6, wherein:
each of the sensors is a flat plate semiconductor sensor having a sensitive surface; and
when a main measurement direction is defined as a direction which is orthogonal to the right-left direction and to which the tip portion is directed, and when a tip portion thickness direction is defined as a direction which is orthogonal to the right-left direction and the main measurement direction, the sensitive surface of each sensor is directed to the right-left direction or the tip portion thickness direction.

11. The survey meter according to claim 10, wherein the plurality of sensors are layered in the right-left direction.

12. The survey meter according to claim 10, wherein the plurality of sensors are arranged in the right-left direction such that the sensitive surfaces thereof are directed to the tip portion thickness direction.

13. The survey meter according to claim 6, wherein:
said plurality of sensors arranged in the right-left direction include a plurality of flat plate detectors stacked side-by-side in a right-left direction.

14. The survey meter according to claim 1, wherein there is provided a control section which selects, from a plurality of sensors, one or more sensors which are caused to perform detection operation according to an amount of radiation.

15. The survey meter according to claim 14, wherein the control section changes the number of sensors caused to perform detection operation according the amount of the radiation.

* * * * *